United States Patent
Tuen

(10) Patent No.: US 6,752,788 B2
(45) Date of Patent: Jun. 22, 2004

(54) SYRINGE NEEDLE COVER

(76) Inventor: Yu Ying Tuen, Letter Box 16, Ling Tong Mei Village, Sheung Shui, N.T. (HK)

( * ) Notice: Subject to any disclaimer, the term of this patent is extended or adjusted under 35 U.S.C. 154(b) by 0 days.

(21) Appl. No.: 10/165,993

(22) Filed: Jun. 10, 2002

(65) Prior Publication Data

US 2003/0028150 A1 Feb. 6, 2003

(30) Foreign Application Priority Data

Jul. 31, 2001 (CN) ........................ 01231198 U

(51) Int. Cl.[7] ............................ A61M 5/00; A61M 5/32
(52) U.S. Cl. ........................ 604/192; 604/110
(58) Field of Search ................. 604/192–198, 604/263, 110

(56) References Cited

U.S. PATENT DOCUMENTS

| | | | |
|---|---|---|---|
| 1,779,451 A | * 10/1930 | Sponsel | ........................ 604/197 |
| 5,188,611 A | * 2/1993 | Orgain | ........................ 604/192 |
| 5,232,455 A | 8/1993 | Hollister | |
| 5,509,907 A | 4/1996 | Bevilacqua | |
| 5,615,771 A | * 4/1997 | Hollister | ........................ 604/263 |
| 6,298,541 B1 | * 10/2001 | Newby et al. | ........................ 604/192 |

FOREIGN PATENT DOCUMENTS

CN 2314803 4/1999

* cited by examiner

*Primary Examiner*—Brian L. Casler
*Assistant Examiner*—Matthew DeSanto
(74) *Attorney, Agent, or Firm*—Clock Tower Law Group; Erik J. Heels; Joshua D. Mather

(57) ABSTRACT

The invention is a syringe needle Protection Cover, including a Needle Hub to secure the needle base and a side-opening cover with an Axial Slot to protect the needle. The needle is at the center of the needle base, and a Longitudinal Member forms a side-opening cover that integrates with the Needle Hub at one side via a Hinge. The Longitudinal Member opens easily and locks closed securely. When the Protection Cover is in the closed position, it is difficult to force open, thus making it difficult to reuse a needle. The protection cover gives users more than one visual indication that a needle has been used, locks in a closed position with multiple locking structures, and after use, deforms the needle so as to render it non-reusable.

1 Claim, 7 Drawing Sheets

SYRINGE NEEDLE COVER

CROSS REFERENCE TO RELATED APPLICATIONS

Applicant claims priority of Chinese application in the name of TUEN, Yu Ying, filing number 01231198.7, filed Jul. 7, 2001, issued Mar. 1, 2002.

BACKGROUND OF THE INVENTION

1. Field of the Invention

The invention relates to protection covers for syringe-type needles, including syringe needles used for medical treatment, dentistry, veterinary treatment, and laboratory work, and including needles such as subcutaneous syringe needles, intravenous syringe needles, LUER-LOK type syringe needles, and hemospasia syringe needles.

2. Description of Prior Art

Many pathogens are known to be transmitted by needle-stick injuries. As such, the prior art includes a large number of needle packaging structures designed to prevent such injuries. Injection molding processes allow for the manufacture of single-piece disposable needle packaging structures. Disposable syringe needles generally include a needle, a syringe, and a protection cover. For disposable syringe needles commonly used in hospitals or other medical institutions, the protection cover is often detached from the syringe needle and set aside just before the needle is used to administer an injection. The protection cover is set aside while the needle is being used to administer an injection and is then reattached after the injection. As such, it is possible for the protection cover to be lost or for bystanders, such as members of the medical staff, to be accidentally punctured by the uncovered needle.

The unprotected needle creates disposal problems. The sanitation requirements and operational rules of institutions that use disposable syringe needles require such needles to be discarded after use. It is necessary to ensure that a protection cover protects each used needle before the needle is discarded. Protection covers, however, can get lost, and, as such, syringe needles are sometimes discarded without any protection covers or without properly attached protection covers. These unprotected needles may lead to the spread of infectious diseases that spread via blood, such as AIDS or hepatitis.

Efforts to solve these problems include a number of patents. Chinese Patent CN2314803 (Lin Shao Shan, filed Dec. 25, 1997, published Apr. 4, 1999) discloses a side-opening syringe needle protection cover, including a protection cover to protect the needle and a needle hub that integrates with a needle base, with a side slot on the protection cover. When the protection cover is closed, the needle is within the side slot, and the protection cover can be opened horizontally to expose the needle. When the injection is over, the protection cover can be closed to enclose the needle. There are protruding U-shaped brims at the bottom of the protection cover, and there are side blocks at the two sides of the needle hub. On top of the side blocks are notches that interlock with outward protrusions, securing the needle in the side slot when the protection cover is closed, and the needle can be exposed for use when the protection cover is opened.

The CN2314803 side-opening syringe needle protection cover solves some problems. The cover can solve the problem of losing the protection cover. The protection cover can be opened and closed with one hand while avoiding accidental puncturing. The locking structure allows a user to horizontally bend the protection cover to expose the needle for injection and to close the cover after use. However, a problem arises because the protection cover can be reopened after enclosing the needle. If a used needle is not properly discarded, it may not be possible for members of the medical staff to recall whether or not the needle has been used, which could lead to the reuse of a needle. Even worse, different medicines could be inadvertently mixed in the syringe, which may cause sanitation problems, patient injury, or death. All of these problems must be avoided.

U.S. Pat. No. 1,779,451 (Sponsel, Oct. 28, 1930) discloses a Hypodermic-syringe Guard. While Sponsel discloses a bendably attached slotted protective needle cover, the '451 needle guard does not give any indication whether or not a needle has been used.

U.S. Pat. No. 5,188,611 (Orgain, Feb. 23, 1993) discloses a Safety Sheath For Needles, Sharp Instruments And Tools. The safety sheath includes a number of different mechanisms for unsheathing and resheathing a needle. The '611 safety sheath is specifically designed so that it can be used repeatedly (column 2, lines 63–64). Furthermore, Orgain discloses the importance of a locking mechanism that will not damage the needle during resheathing (column 2, lines 29–33). However, for disposable syringe needles, the needle should not be reused, and it is desirable to have the needle damaged to prevent reuse of the needle.

U.S. Pat. No. 5,232,455 (Hollister, Aug. 3, 1993) discloses a Syringe With Protective Housing that exhibits a number of disadvantages associated with the prior art. While Hollister discloses a bendably attached slotted protective needle cover, the '455 protective housing does not give the user visual indications that the needle has been used. As such, the unused needle covered by this protective housing looks just like the used needle covered by this protective housing. U.S. Pat. No. 5,509,907 (Bevilacqua, Apr. 23, 1996) discloses a Syringe Needle Guard Assembly that exhibits the same disadvantages as the '455 housing.

None of the above prior art discusses syringe needle protection covers that give users more than one visual indication that a needle has been used. What is needed, therefore, is a syringe needle protection cover that overcomes the above-mentioned limitations, namely a protection cover that 1) gives users more than one visual indication that a needle has been used, 2) locks in a closed position with multiple locking structures, and 3) after use, deforms the needle so as to render it nonreusable.

BRIEF SUMMARY OF THE INVENTION

The present invention is a syringe needle protection cover. The protection cover prevents a user from mistakenly reusing a syringe needle. The protection cover has a longitudinal member with an axial slot and is connected to a needle hub by a hinge. The unopened cover suppresses a latch. Opening the cover to use the needle releases the latch. After the initial release of the latch, the latch prevents the cover from returning to an erect position. The cover returns to enclose the needle but in a bent/diagonal position relative to the syringe body. After resheathing the needle, a locking bar engages on the needle. Closing the cover bends the needle once, and the locking bar bends the needle a second time if and when the cover is reopened. The bent cover and the bent needle provide two indications that the needle is used.

Objects

Multiple Locking Structures

One object of the invention is to have a needle cover that locks in a closed position with multiple locking structures.

Needle Deformation

Another object of the invention is to have a needle cover that deforms the needle after use to render it non-reusable.

Visual Indications of Needle Use

Another object of the invention is to have a needle cover that gives users more than one visual indication that a needle has been used, thereby reducing the likelihood that a needle will be reused.

Features

Multiple Locking Structures

One feature of the invention is that it has multiple locking structures that make it difficult to re-open the Longitudinal Member after it has been closed.

This syringe needle Protection Cover includes a Needle Hub to secure a needle and a side-opening Longitudinal Member with an Axial Slot that covers and protects the needle. The needle is at the center of the Needle Hub. The Longitudinal Member integrates with the Needle Hub at one side via a Hinge, and has two U-shaped Brims that are oriented at a right angle to each other, that protrude outward, and that are separated by a Slot. There are Side Blocks at the two sides of the Needle Hub. On the Side Blocks are Locking Protrusions, and below the Locking Protrusions are Flukes.

The first locking structure is releasable. Before the needle is used, the Protection Cover is held closed in a erect position by the interlocking of the Detents on the Longitudinal Member with the Locking Protrusions on the Side Blocks.

The second locking structure is non-releasable. After the needle is used, the Protection Cover locks closed in a diagonal position by the interlocking of the Locking Protrusions on the Longitudinal Member with the Flukes on the Side Blocks of the Needle Hub. The Protection Cover can be closed in a diagonal position because the Needle Hub has a sloping or sunken Upper Surface below a Hinge that connects the Longitudinal Member to the Needle Hub.

The third locking structure is also non-releasable. The Needle Hub has a Front Block with Locking Protrusions that correspond to and interlock with Slots on the inside bottom of the Longitudinal Member. After the needle is used, the Protection Cover is locked closed in diagonal position by the interlocking of the Locking Protrusions on the Front Block with the Slots on the Longitudinal Member.

The fourth locking structure is also non-releasable. Within the Axial Slot of the Longitudinal Member, there is at least one pair of Locking Bars that extend diagonally from the inside surface of the Longitudinal Member, and that, when viewing the Longitudinal Member along its long axis, form intersections. When the Longitudinal Member is resheathed after use, the needle goes through the Locking Bars and enters the space between the Locking Bars and the inside surface of the Longitudinal Member, so that even if the Longitudinal Member is forcibly reopened, the needle inside is deformed when going through the intersecting Locking Bars. This further reduces the possibility that the needle will be reused.

Many variations on the locking structures are possible. For example, for the first locking structure, the Detents and the Locking Protrusions could be reversed so that the Detents would be on the Side Blocks and the Locking Protrusions would be on the Longitudinal Member. Another example is that the Slots on the Longitudinal Member can be formed in a triangular, rectangular, or other shape. Another example is that the first locking structure could be a breakable plastic strip or band. Similar variations are possible with the other locking structures and should be readily apparent to those skilled in the art.

Needle Deformation

Another feature of the invention is that the needle cover deforms the needle to prevent reuse.

The needle is deformed, bent, or otherwise damaged as a result of the operation of the fourth locking structure. As discussed above, when the Longitudinal Member is closed after use, the needle goes through the Locking Bars and enters the space between the Locking Bars and the inside surface of the Longitudinal Member. The needle can be deformed in more than one way. When the Longitudinal Member closes and interlocks with the Needle Hub in the diagonal position, the needle presses against the inside wall of the Longitudinal Member and bends. Additionally, even if the Longitudinal Member is forcibly reopened, the needle inside is deformed again when going through the intersecting Locking Bars.

Visual Indications of Needle Use

Another feature of the invention is that after the needle is used and the cover is closed, the bent needle and the bent cover provide two indications that the needle has been used.

Advantages

There are many advantages to the invention, including the following. Other advantages, applications, and variations of the invention will be apparent to those skilled in the art. For example, the invention is not limited to syringe needles but can be adapted to be a Protection Cover for any number of devices, medical or otherwise.

Multiple Locking Structures

The advantages of having multiple locking structures include the following. With multiple locking structures, the Longitudinal Member is less likely to be reopened after use, thereby making it less likely that a needle will be reused. Multiple locking structures also make the entire Protection Cover stronger and less likely to be reopened.

Needle Deformation

The advantages of having the needle deformed after use include the following. When the needle is deformed, bent, or otherwise damaged, it is less likely that the needle will be reused. The needle can be deformed as a result of the initial closing of the Longitudinal Member and any subsequent forcible reopening of the Longitudinal Member. Even if the Longitudinal Member is forcibly reopened after having been closed, the Locking Bars sufficiently damage the needle to prevent its reuse. The dimensions of the Locking Bars are varied appropriately to accommodate a variety of sizes of needles.

Visual Indications of Needle Use

The advantages of having visual indications of needle use include the following. Before the needle is used, the Longitudinal Member closes in an erect position relative to the Needle Hub. After the needle is used, the Longitudinal Member closes in a diagonal position relative to the Needle Hub. The diagonal position provides a visual indication that the needle is used. Additionally, the fourth locking structure discussed above deforms the needle (either upon initial closing of the Longitudinal Member, subsequent reopening, or both), which provides an additional indication that the needle has been used. The multiple visual indications of needle use make it less likely that a needle will be reused.

DETAILED DESCRIPTION OF THE INVENTION, INCLUDING THE PREFERRED EMBODIMENT

The following is a detailed description of the Protection Cover according to the invention with reference to FIGS. 1–7.

Figure 1:
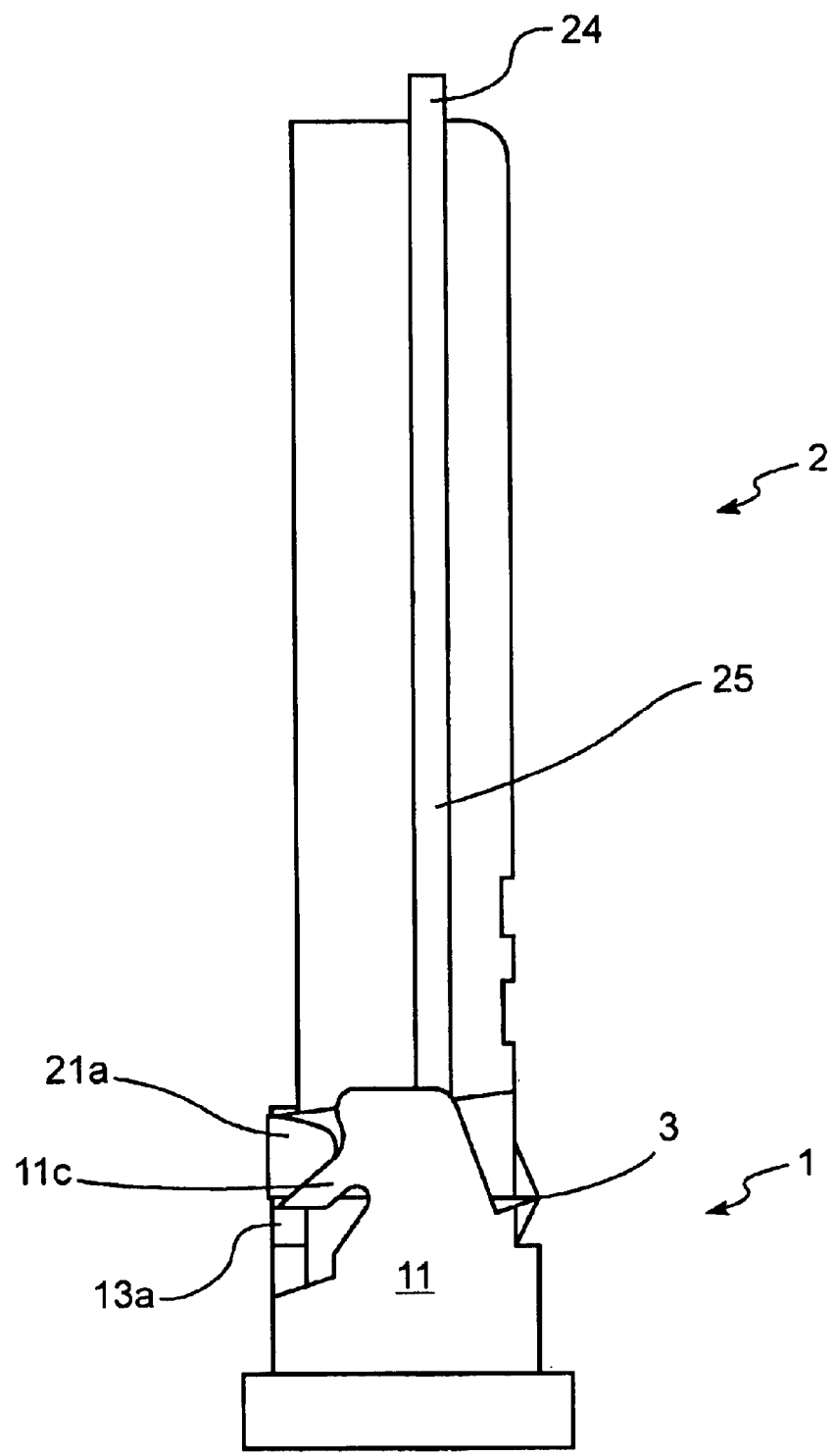
FIG. 1 is the side view of the Protection Cover shown in the erect position before the needle is used.
Figure 2:
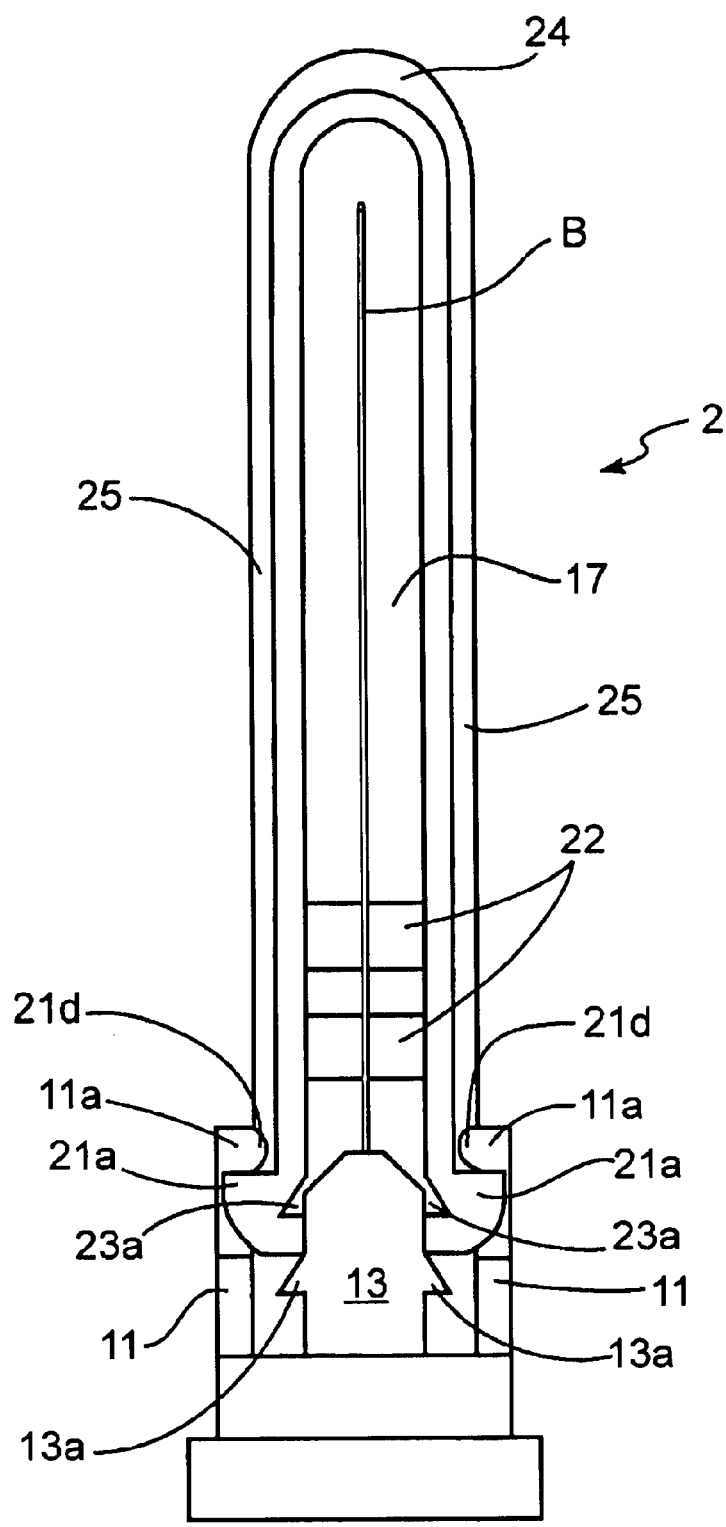
FIG. 2 is the front view of the Protection Cover shown in the erect position before the needle is used. The position of the needle is also indicated.

As indicated in FIG. 1 and FIG. 2, the Protection Cover includes a Needle Hub 1 and a Longitudinal Member 2. The Needle Hub 1 is used to secure the base of a syringe needle (not indicated), and the Longitudinal Member 2 is used to cover and protect a needle such as a Cannula Needle B. Typically, the Cannula Needle B is at the center of the needle base (not indicated). The Protection Cover has a Hinge 3, which integrates with the Longitudinal Member 2 at the back side of the Needle Hub 1. U-shaped Brim 21b has two Locking Protrusions 21a at the lower part of the Longitudinal Member 2 (see FIG. 4). There are Side Blocks 11 at the two sides of the Needle Hub 1 and on top of the Side Blocks 11 are Locking Protrusions 11a corresponding to and that interlock with Detents 21d on the outside of the Longitudinal Member 2. The Locking Protrusions 11a are optimized to be knob-shaped protrusions (see FIG. 3). The Needle Hub 1 has a sloping or sunken Upper Surface 14 from Hinge 3 (see FIG. 3), which provides space for the Longitudinal Member 2 to bend beyond the erect position to a diagonal position relative to the Needle Hub 1. On the front side of each Side Block 11 there are Flukes 11c that can be buckled with the Locking Protrusions 21a (lower than the Locking Protrusions 11a). Thus, when the Longitudinal Member 2 is at the erect position as indicated in FIG. 1 or FIG. 2 (i.e. before use of the needle), the Longitudinal Member 2 is buckled with the Needle Hub 1 via the Locking Protrusions 11a and the corresponding Detents 21d, enabling the Longitudinal Member 2 to maintain an approximately perpendicular opened position.

Figure 3:
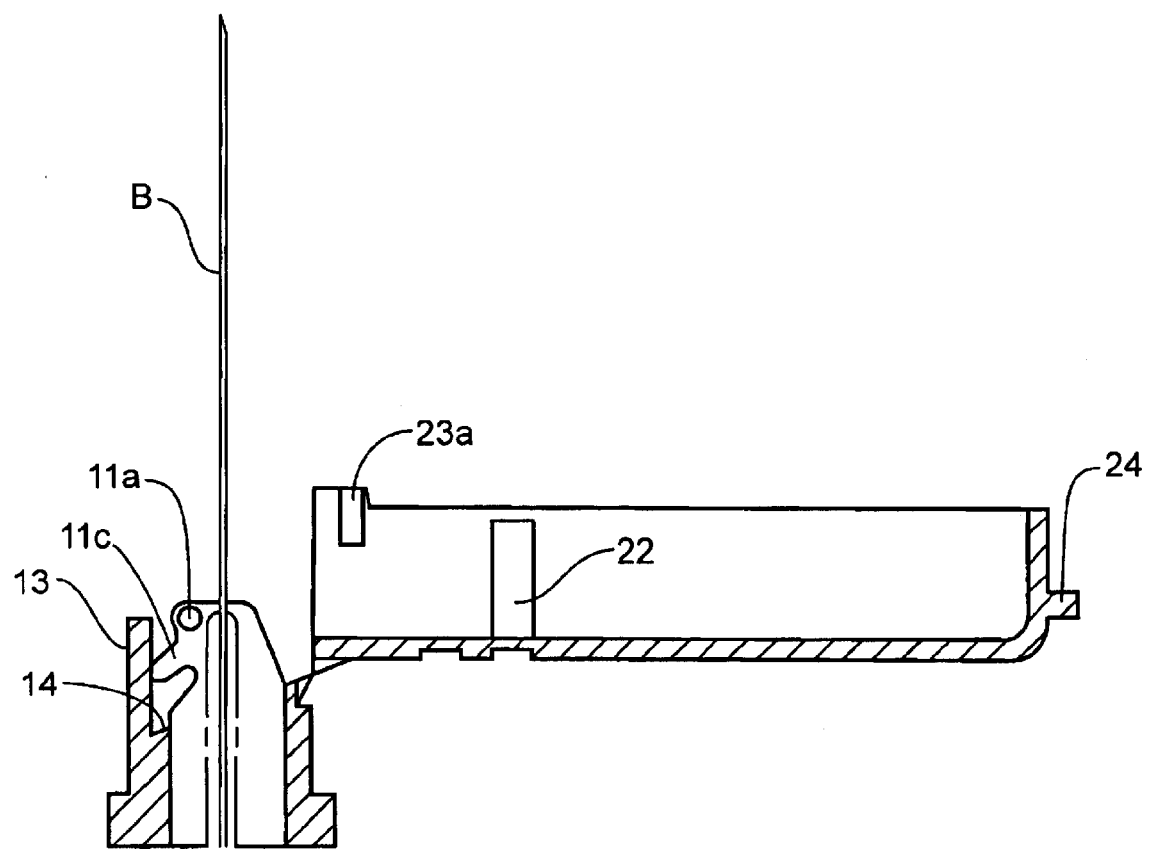
FIG. 3 is the side sectional view of the Protection Cover shown at the opened position. The position of the needle is also indicated.
Figure 4:
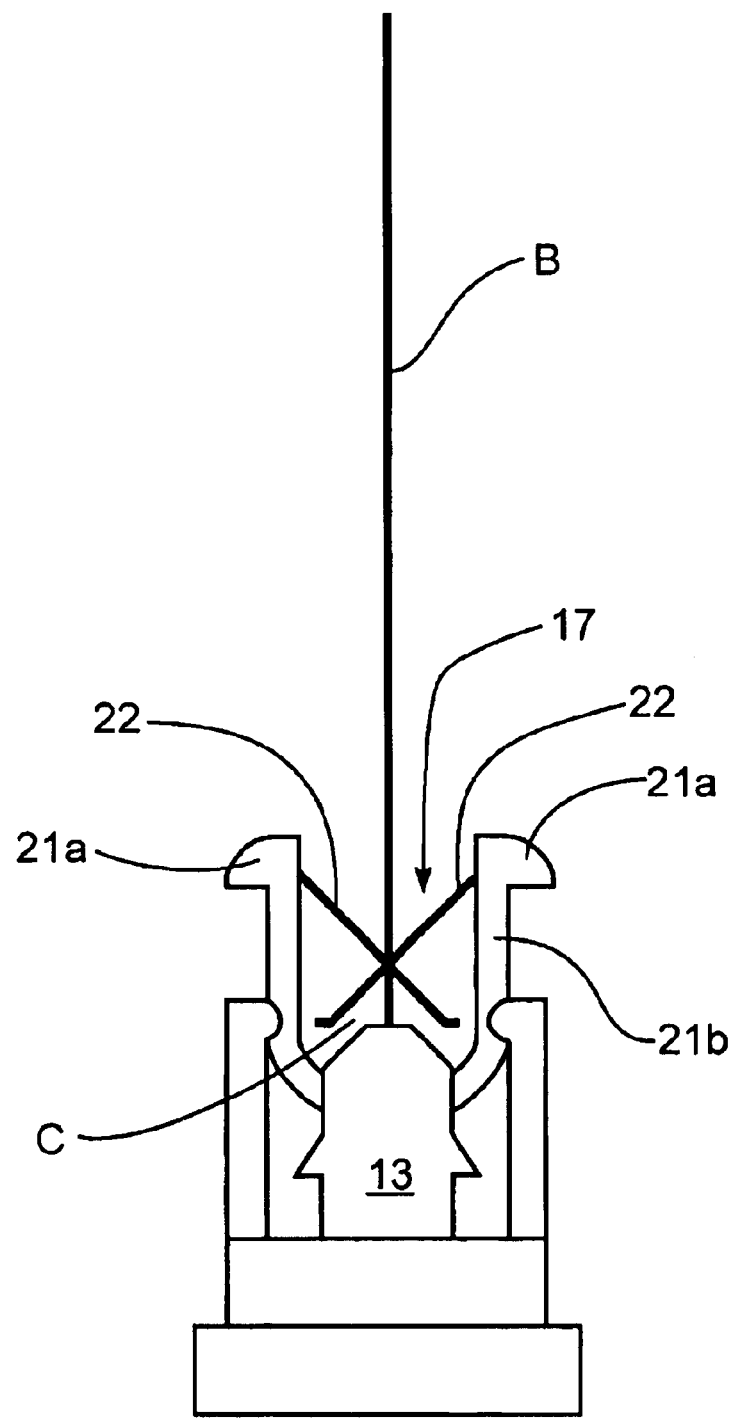
FIG. 4 is the front view of FIG. 3.

During use of the needle, as indicated in FIG. 3 and FIG. 4, the Longitudinal Member 2 rotates about the Hinge 3 to open, thus exposing the Cannula Needle B. After the needle has been used and when the Longitudinal Member 2 is closed, the Longitudinal Member 2 moves beyond the original erect position to the diagonal position indicated in FIG. 5 and FIG. 6. For example, one can press the Longitudinal Member 2 to the surface of a desk or other hard surface to bend it, making it lock into the diagonal position by the interlocking of the Flukes 11c with the Locking Protrusions 21a, thus ensuring that the needle inside cannot be reused. With the Protection Cover now having a noticeably bent shape after use, the problem of mistakenly taking out the used needle can be avoided.

Moreover, the locking structures at the erect position (i.e. the Locking Protrusions 11a and the Detents 21d) and at the diagonal position (i.e. the Locking Protrusions 21a and Flukes 11c) are different. The locking structure at the erect position before the initial opening (i.e. the Locking Protrusions 11a and the Detents 21d) makes the Longitudinal Member 2 easier to open, and the locking structure after the Longitudinal Member 2 is closed (i.e. the Locking Protrusions 21a and Flukes 11c) is an nonreleasable fixed locking structure, which is the first security structure of the Protection Cover.

Figure 5:
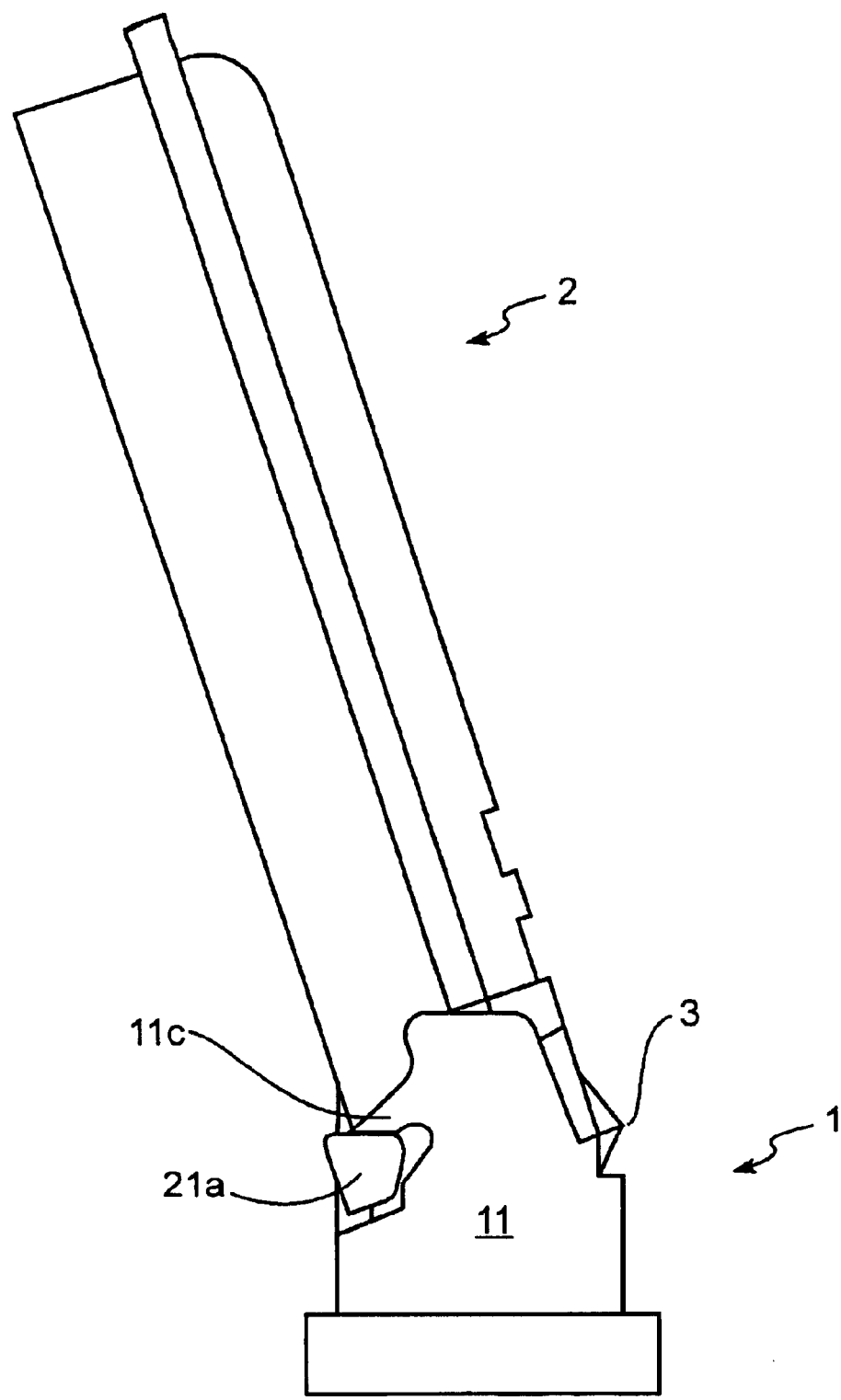
FIG. 5 is the side view of the Protection Cover shown in the diagonal position after the needle is used.
Figure 6:
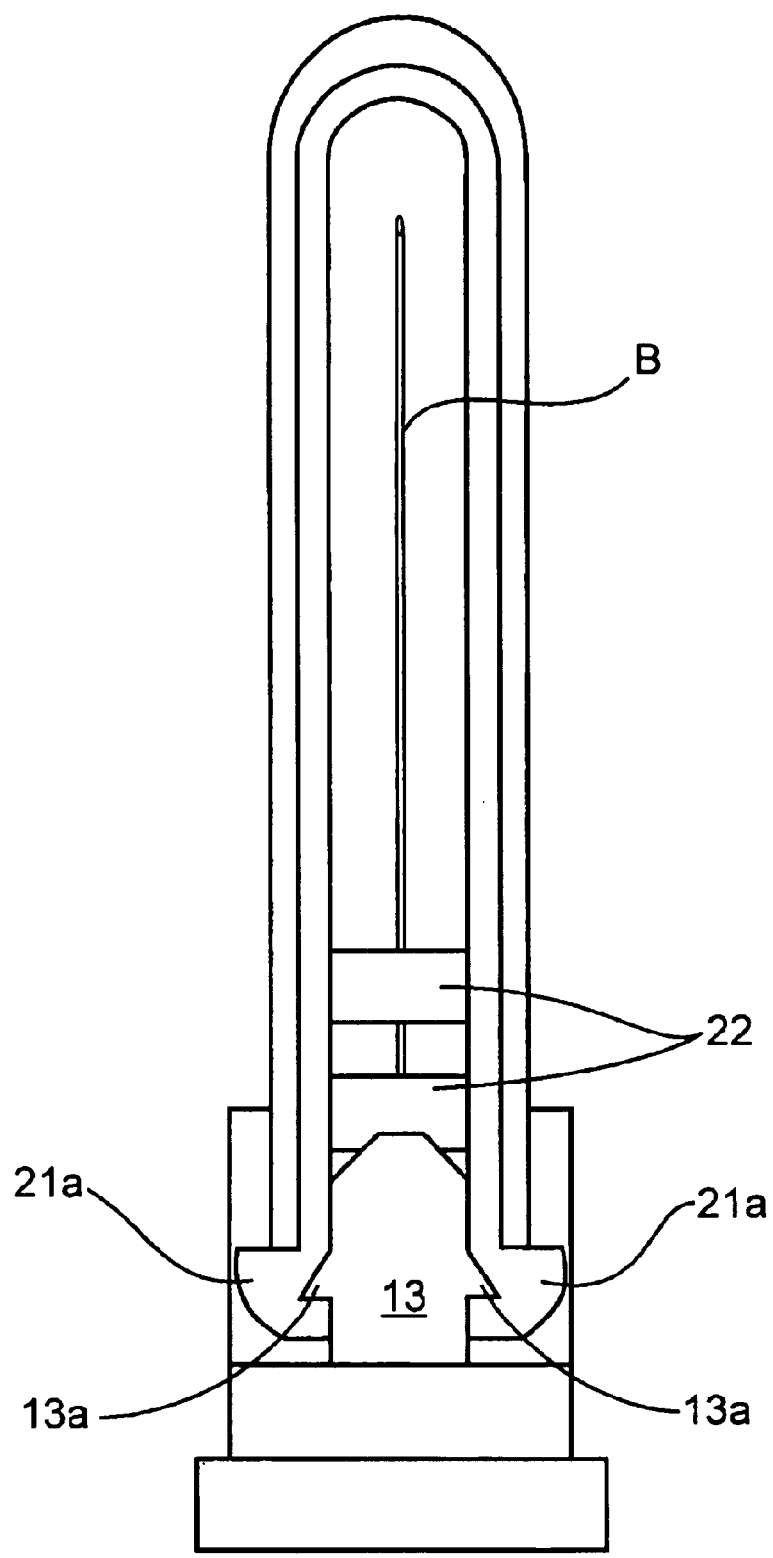
FIG. 6 is the front view of FIG. 5. The position of the needle is indicated, but the position of the needle base is not indicated.
Figure 7:
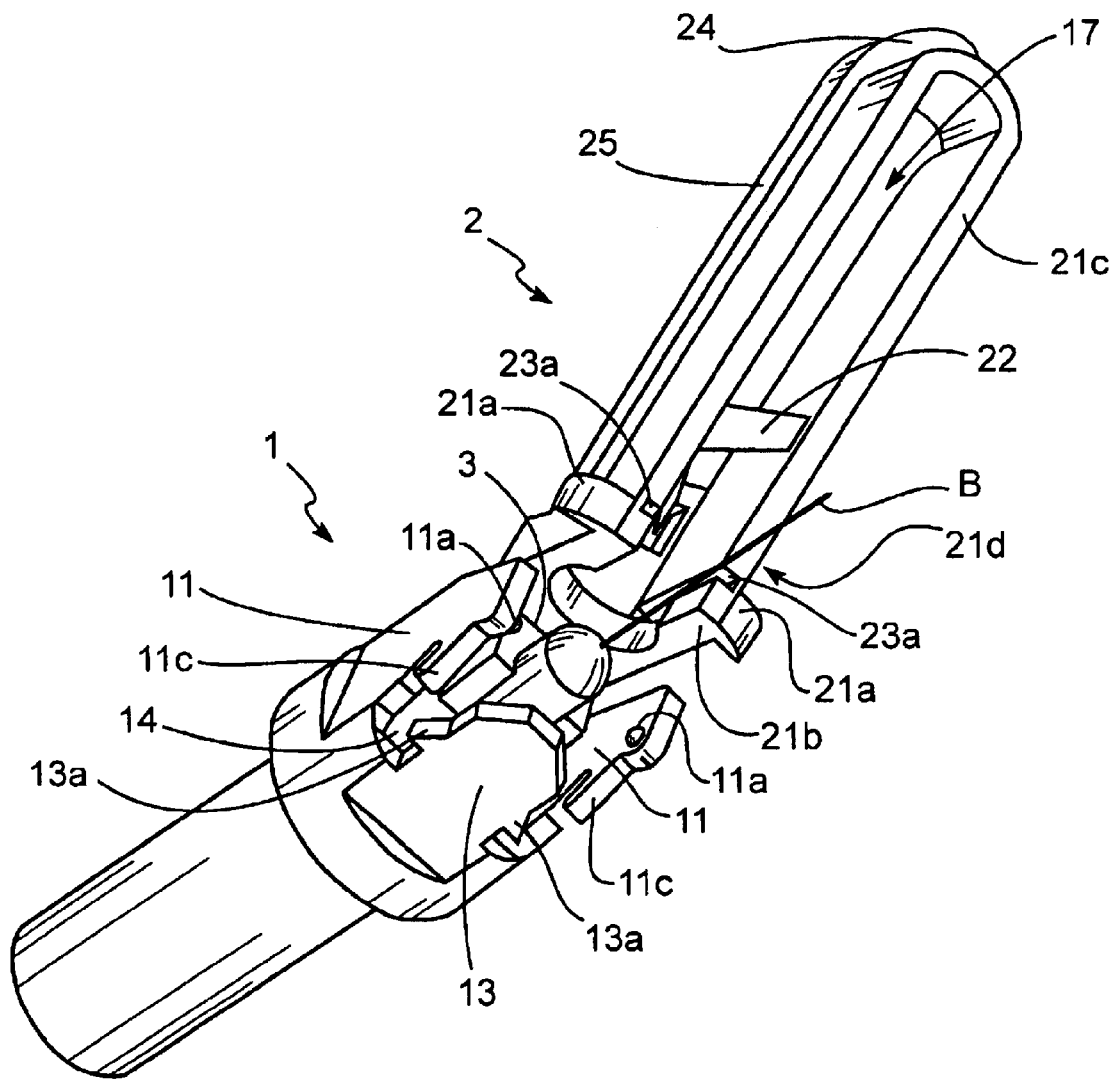
FIG. 7 is a three-dimensional view of the needle cover shown in the opened position with a needle inside.

In reference to FIG. 1 and FIG. 2, the Protection Cover has a Front Block 13 opposite from the Hinge 3. The Front Block 13 has Locking Protrusions 13a lower than the Flukes 11c, and at the bottom of the Longitudinal Member 2 there are Slots 23a corresponding to the Locking Protrusions 13a. When the Longitudinal Member 2 is closed after use, the Locking Protrusions 13a interlock with the Slots 23a to form a second security structure of the Protection Cover. This second security structure ensures that the Longitudinal Member 2 cannot be re-opened after being bent into the locked position (as indicated in FIG. 5 and FIG. 6).

Referring to FIG. 2, FIG. 3, and FIG. 4, there is at least one pair of Locking Bars 22 within the Axial Slot 17 of the Longitudinal Member 2. The Locking Bars 22 extend from the inside surface of the Longitudinal Member 2 to form intersections. When the Longitudinal Member 2 is closed after use, as indicated in FIG. 5 and FIG. 6, the Canuula needle B goes through the Locking Bars 22 and enters the Space C between the Locking Bars 22 and the inside surface of the Longitudinal Member 2 (see FIG. 4). As indicated in FIG. 6, the Cannula Needle B is between the Locking Bars 22 and the inside surface of the Longitudinal Member 2. Thus, even if the Longitudinal Member 2 is forcibly reopened, the needle inside is damaged when it passes through the intersecting Locking Bars 22. This is the third security structure of the Protection Cover, which allows the medical staff to notice the bent needle and avoid reusing it.

There is also a Tab 24 on top of the Longitudinal Member 2 and/or 0.5–1.2 mm Brims 25 (with an optimized height of 0.8 mm) at the sides of the Longitudinal Member 2. Either of the Tab 24 and Brims 25 makes it easier to open the Longitudinal Member 2 with one's hands and makes the Protection Cover less likely to slip out of one's hands. Moreover, the length and size of the Protection Cover is adapted to conform to the size of the syringe (such as a hypodermic medical needle syringe).

The Protection Cover is ideally formed by injection molding so that it can be a formed from a single piece of plastic. The explanations and descriptions of the invention have been made with reference to the preferred embodiment of the invention. However, it should be understood that the invention is not limited to the various specific details herein but that it can have changes and modifications. For example, the Protection Cover can integrate with the Needle Hub 1 via ultrasonic or embedded mold. The Protection Cover can also integrate with the base of the needle and the syringe by, for example, incorporating grooves or the like into the Needle Hub 1.

I claim:

1. A method for preventing a syringe needle from being reused, said syringe needle having a needle and a syringe, comprising the steps of:

a. providing a syringe needle cover including:

a needle hub adapted to engage said syringe and said needle;

a longitudinal member hingedly connected to said needle hub, and adapted to cover said needle, and having a front side with an axial slot wider and longer than said needle, said longitudinal member assuming an erect position longitudinally enclosing said needle prior to use of said needle, an opened position hingedly rotated away from said needle and exposing said needle for use, and a diagonal position bendably enclosing said needle after use of said needle; and locking means for securing said longitudinal member in said diagonal position after use of said needle so that said longitudinal member cannot be moved from said diagonal position, thereby preventing said needle from being re-exposed and re-accessed;

b. uncoupling said longitudinal member from said needle hub;

c. rotating said longitudinal member from said needle hub to an open position to expose said needle for use;

d. rotating said longitudinal member from said open position to said diagonal position; and e. engaging said locking means to securely lock said longitudinal member with said needle hub so that said longitudinal member cannot thereafter be moved from said diagonal position thereby preventing said syringe needle cover from being reopened.

* * * * *